(12) United States Patent
Wang

(10) Patent No.: US 9,013,555 B2
(45) Date of Patent: Apr. 21, 2015

(54) METHOD AND APPARATUS FOR ULTRAHIGH SENSITIVE OPTICAL MICROANGIOGRAPHY

(75) Inventor: Ruikang Wang, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 13/577,857

(22) PCT Filed: Feb. 8, 2011

(86) PCT No.: PCT/US2011/024069
§ 371 (c)(1),
(2), (4) Date: Aug. 8, 2012

(87) PCT Pub. No.: WO2011/097631
PCT Pub. Date: Aug. 11, 2011

(65) Prior Publication Data
US 2012/0307014 A1 Dec. 6, 2012

Related U.S. Application Data

(60) Provisional application No. 61/302,409, filed on Feb. 8, 2010.

(51) Int. Cl.
*H04N 13/02* (2006.01)
*A61B 5/05* (2006.01)
*A61B 6/00* (2006.01)
(Continued)

(52) U.S. Cl.
CPC ............... *A61B 3/102* (2013.01); *A61B 5/0066* (2013.01); *A61B 5/0261* (2013.01); *A61B 5/444* (2013.01)

(58) Field of Classification Search
None
See application file for complete search history.

(56) References Cited

U.S. PATENT DOCUMENTS 4,131,022 A * 12/1978 Mezrich .......................... 73/606
6,549,801 B1    4/2003 Chen
(Continued)

FOREIGN PATENT DOCUMENTS

| WO | WO2004043245 A  | 5/2004 |
| WO | WO2008039660 A2 | 4/2008 |
| WO | WO2010129494 A2 | 11/2010 |

OTHER PUBLICATIONS

Yasuno, Y. et al., "Simultaneous B-M-Mode Scanning Method for Real-Time Full-Range Fourier Domain Optical Coherence Tomography," Applied Optics, OSA, Optical Society of America, 2006, pp. 1861-1865.

(Continued)

*Primary Examiner* — Frederick Bailey
(74) *Attorney, Agent, or Firm* — Schwabe, Williamson & Wyatt

(57) ABSTRACT

Embodiments herein provide an ultrahigh sensitive optical microangiography (OMAG) system that provides high sensitivity to slow flow information, such as that found in blood flow in capillaries, while also providing a relatively low data acquisition time. The system performs a plurality of fast scans (i.e., B-scans) on a fast scan axis, where each fast scan includes a plurality of A-scans. At the same time, the system performs a slow scan (i.e., C-scan), on a slow scan axis, where the slow scan includes the plurality of fast scans. A detector receives the spectral interference signal from the sample to produce a three dimensional (3D) data set. An imaging algorithm is then applied to the 3D data set in the slow scan axis to produce at least one image of the sample. In some embodiments, the imaging algorithm may separate flow information from structural information of the sample.

17 Claims, 10 Drawing Sheets

(51) Int. Cl.
G06K 9/48 (2006.01)
G01N 9/24 (2006.01)
A61B 3/10 (2006.01)
A61B 5/026 (2006.01)
A61B 5/00 (2006.01)

(56) References Cited

U.S. PATENT DOCUMENTS

| | | | |
|---|---|---|---|
| 8,180,134 | B2 | 5/2012 | Wang |
| 2003/0101820 | A1* | 6/2003 | Siong ............................ 73/607 |
| 2003/0199769 | A1 | 10/2003 | Podoleanu |
| 2003/0199796 | A1 | 10/2003 | Yamazaki et al. |
| 2003/0220749 | A1 | 11/2003 | Chen et al. |
| 2005/0004453 | A1 | 1/2005 | Tearney et al. |
| 2005/0140984 | A1 | 6/2005 | Hitzenberger |
| 2005/0171438 | A1 | 8/2005 | Chen et al. |
| 2005/0253055 | A1* | 11/2005 | Sprague et al. ............... 250/234 |
| 2006/0270929 | A1 | 11/2006 | Bouma et al. |
| 2008/0025570 | A1 | 1/2008 | Fingler et al. |
| 2009/0225324 | A1* | 9/2009 | Bernstein et al. ............. 356/479 |
| 2009/0226096 | A1* | 9/2009 | Namai et al. .................. 382/199 |
| 2010/0027857 | A1 | 2/2010 | Wang |
| 2012/0063665 | A1 | 3/2012 | Wang |

OTHER PUBLICATIONS

Wojtkowski, M. et al., "Real-time in Vivo Imaging by High-speed Spectral Optical Coherence Tomography," Optics Letters, OSA, Optical Society of America, 2003, vol. 28, No. 19, pp. 1745-1747.

Wojtkowski, M. et al., "In Vivo Human Retinal Imaging by Fourier Domain Optical Coherence Tomography," Journal of Biomedical Optics, SPIE, 2002, vol. 7, No. 3, pp. 457-463.

Shuliang, J. et al., "Simultaneous Acquisition of Sectional and Fundus Ophthalmic Images with Spectral-domain Optical Coherence Tomography," Optics Express, 2005, vol. 13, No. 2, pp. 444-452.

Sarunic, Marinko V. et al., "Real-time Quadrature Projection Complex Conjugate Resolved Fourier Domain Optical Coherence Tomography," Optics Letters, 2006, vol. 31, pp. 2426-2428.

Vakoc, B.J. et al., Elimination of Depth Degeneracy in Optical Frequency-domain Imaging Through Polarization-based Optical Demodulation, Optics Letters, 2006, vol. 31, pp. 362-364.

Bachmann, Adrian H. et al., "Heterodyne Fourier Domain Optical Coherence Tomography for Full Range Probing with High Axial Resolution," Optics Express, 2006, vol. 14, No. 4, pp. 1487-1496.

Ma, Zhen et al., "Arbitrary Three-phase Shifting Algorithm for Achieving Full Range Spectral Optical Coherence Tomography," Chinese Physics Letters, 2006, vol. 23, No. 2, pp. 366-369.

Yasuno, Yoshiaki, et al., "Real Time and Full-Range Complex Fourier Domain Optical Coherence Tomography," Optical and Quantum Electronics, 2005, vol. 37, Nos. 13-15, pp. 1157-1163.

Sarunic, Marinko et al., "Instantaneous Complex Conjugate Resolved Spectral Domain and Swept-source OCT Using 3×3 Fiber Couplers," Optics Express, 2005, vol. 13, pp. 957-967.

Huber, R., et al., "Amplified, Frequency Swept Lasers for Frequency Domain Reflectometry and OCT Imaging: Design and Scaling Principles," Optics Express, 2005, vol. 13, No. 9, pp. 3513-3528.

Gotzinger, Erich et al., "High Speed Full Range Complex Spectral Domain Optical Coherence Tomography," Optics Express, 2005, vol. 13, No. 2, pp. 583-594.

Zhang, Jun, et al., "Full Range Polarization-sensitive Fourier Domain Optical Coherence Tomography," Optics Express, 2004, vol. 12, No. 24, pp. 6033-6039.

Yun, S., et al., "Removing the Depth-degeneracy in Optical Frequency Domain Imaging with Frequency Shifting," Optics Express, 2004, vol. 12, pp. 4822-4828.

Wojtkowski, M. et al., "Full Range Complex Spectral Optical Coherence Tomography Technique in Eye Imaging," Optics Letters, 2002, vol. 27, No. 16, pp. 1415-1417.

Leitgeb, Rainer A. et al., "Phase-shifting Algorithm to Achieve High-speed Long-depth-range Probing by Frequency-domain Optical Coherence Tomography," Optics Letters, 2003, vol. 28, No. 22, pp. 2201-2203.

Hitzenberger, Christoph K., et al., "Differential Phase Measurements in Low-Coherence Interferometry Without 2 pi Ambiguity," Optics Letters, 2001, vol. 26, No. 23, pp. 1864-1866.

Choma, Michael A., et al., "Doppler Flow Imaging of Cytoplasmic Streaming Using Spectral Domain Phase Microscopy," Journal of Biomedical Optics, 2006, vol. 11, No. 2, Article No. 024014.

Seki, J. et al., "Velocity Profiles in the Rat Cerebral Microvessels Measured by Optical Coherence Tomography," Clinical Hemorheology and Microcirculation, 2006, vol. 34, Nos. 1-2, pp. 233-239.

Leitgeb, Rainer A. et al., "Real-time Measurement of in Vitro Flow by Fourier-domain Color Doppler Optical Coherence Tomography," Optics Letters, 2004, vol. 29, No. 2, pp. 171-173.

Leitgeb, Rainer A. et al., "Real-time Assessment of Retinal Blood Flow with Ultrafast Acquisition by Color Doppler Fourier Domain Optical Coherence Tomography," Optics Express, 2003, vol. 11, No. 23, pp. 3116-3121.

Ahn, Yeh-Chan, et al., "Investigation of Laminar Dispersion with Optical Coherence Tomography and Optical Doppler Tomography," Optics Express, 2005, vol. 13, No. 20, pp. 8164-8171.

Zhang, Jun et al., "In Vivo Blood Flow Imaging by a Swept Laser Source Based Fourier Domain Optical Doppler Tomography," Optics Express, 2005, vol. 13, No. 19, pp. 7449-7457.

Pedersen Cameron J., et al., "Phase-referenced Doppler Optical Coherence Tomography in Scattering Media," Optics Letters, 2005, vol. 30, No. 16, pp. 2125-2127.

Vakoc, B.J., et al., "Phase-resolved Optical Frequency Domain Imaging," Optics Express, 2005, vol. 13, No. 14, pp. 5483-5493.

Wang, Ruikang K. et al., "Three-dimensional Optical Microangiography Maps Directional Blood Perfusion Deep Within Microcirculation Tissue Beds in Vivo," Physics in Medicine and Biology, 2007, vol. 52, N531-N537.

Wang, Ruikang K. et al., "Three Dimensional Optical Angiography," Optics Express, 2007, vol. 15, No. 7, pp. 4083-4097.

Wang, Ruikang K. et al., "Doppler Optical Micro-angiography for Volumetric Imaging of Vascular Perfusion in Vivo," Optics Express, 2009, vol. 17, pp. 8926-8940.

An, Lin et al., "In Vivo Volumetric Imaging of Vascular Perfusion Within Human Retina and Choroids with Optical Microangiography," Optics Express, 2008, vol. 16, No. 15, pp. 11438-11452.

An, Lin et al., "Ultrahigh Sensitive Optical Microangiography for in vivo Imaging of Microcirculations Within Human Skin Tissue Beds," Optics Express, 2010, vol. 18, No. 8, pp. 8220-8228.

Fingler, Jeff et al., "Mobility and Transverse Flow Visualization Using Phase Variance Contrast with Spectral Domain Optical Coherence Tomography," Optics Express, 2007, vol. 15, No. 20, pp. 12636-12653.

Zhao, Yonghua et al., "Doppler Standard Deviation Imaging for Clinical Monitoring of in vivo Human Skin Blood Flow," Optics Letters, 2000, vol. 25, No. 18, pp. 1358-1360.

Mariampillai, Adrian et al., "Speckle Variance Detection of Microvasculature Using Swept-Source Optical Coherence Tomography," Optics Letters, 2008, vol. 33, No. 13, pp. 1530-1532.

Fingler, Jeff et al., "Volumetric Microvascular Imaging of Human Retina Using Optical Coherence Tomography with a Novel Motion Contrast Technique," Optics Express, 2009, vol. 17, No. 24, pp. 22190-22200.

* cited by examiner

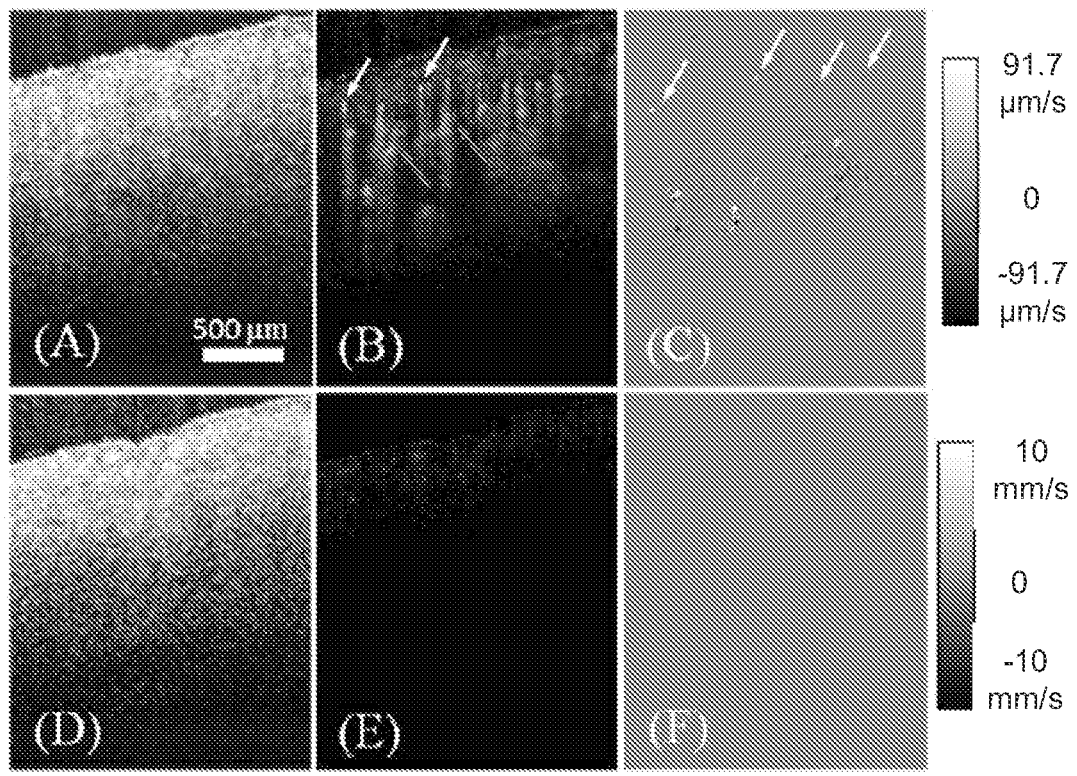
FIGS. 5A-F
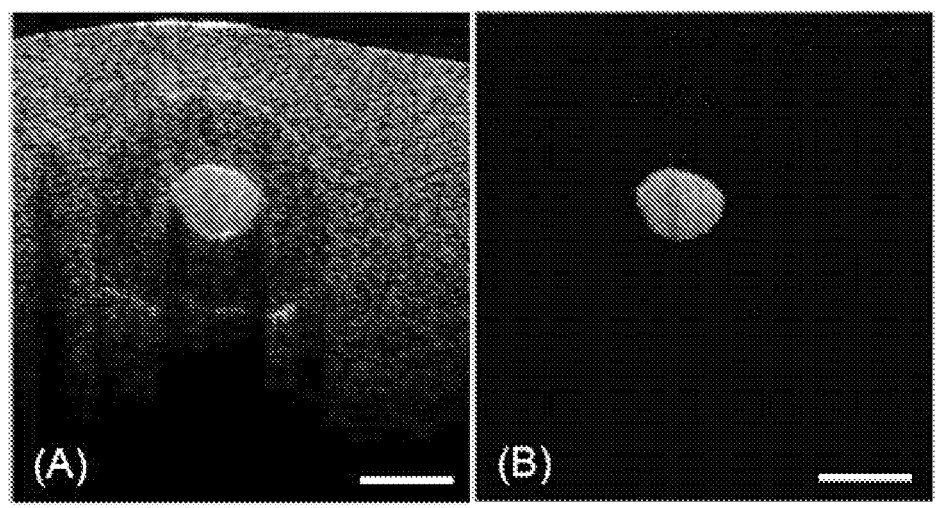
FIGS. 6A-B

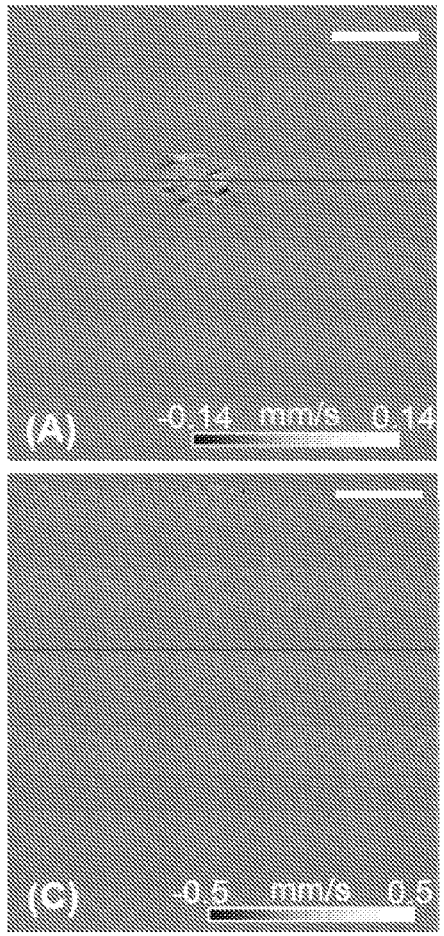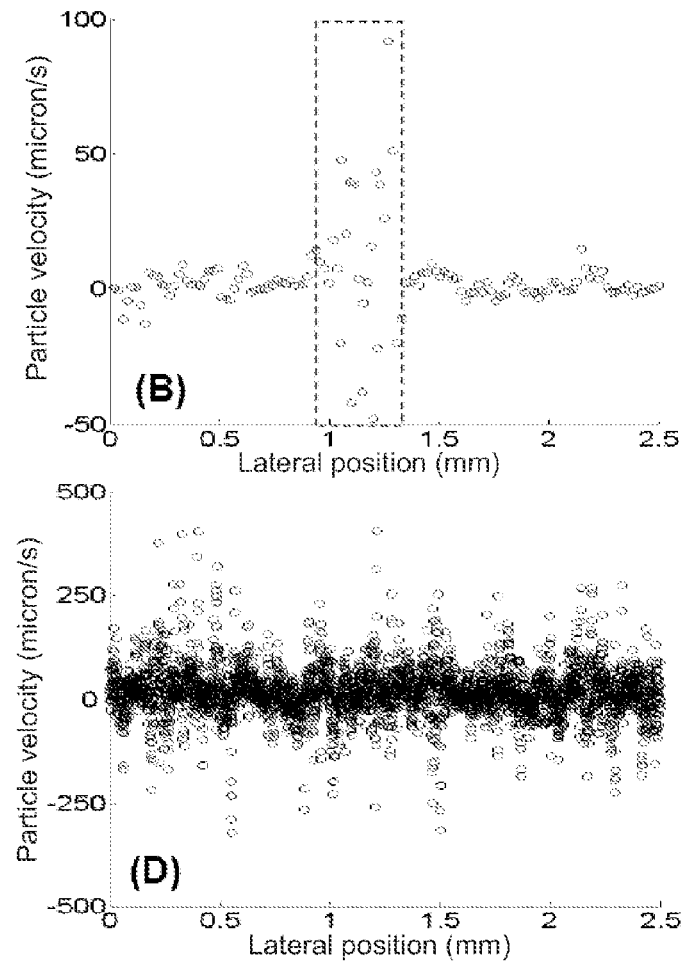
FIGS. 7A-D

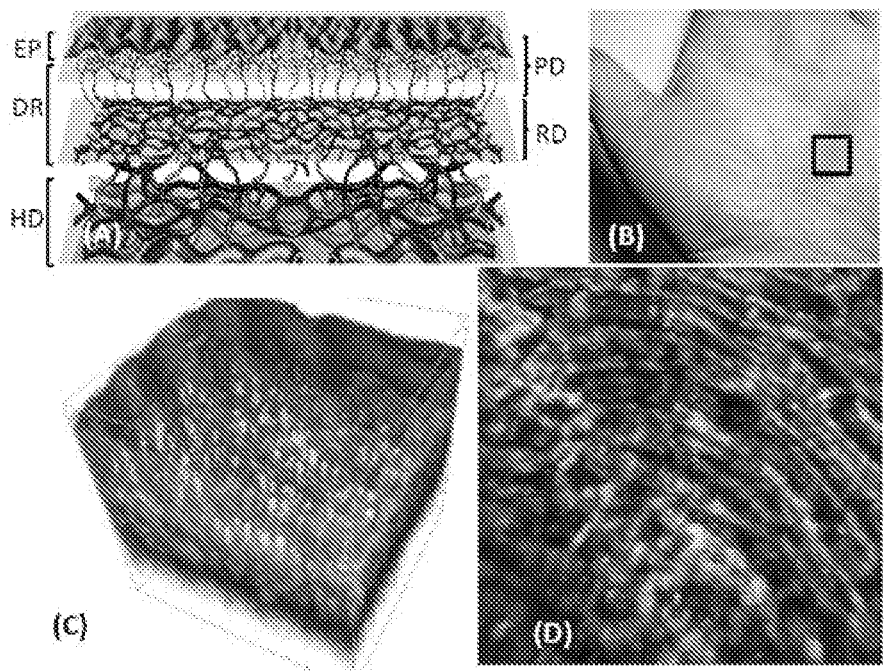
FIGS. 8A-D
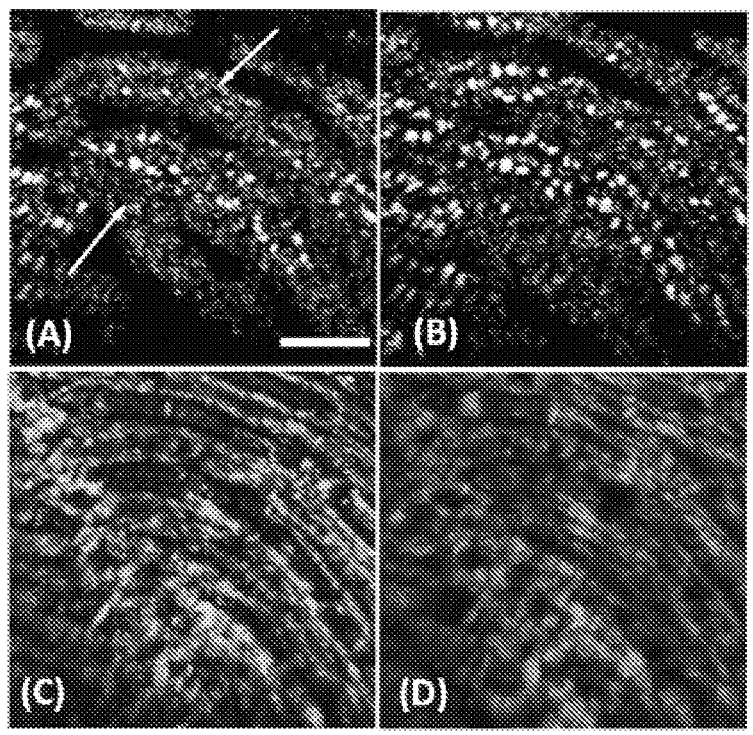
FIGS. 9A-D

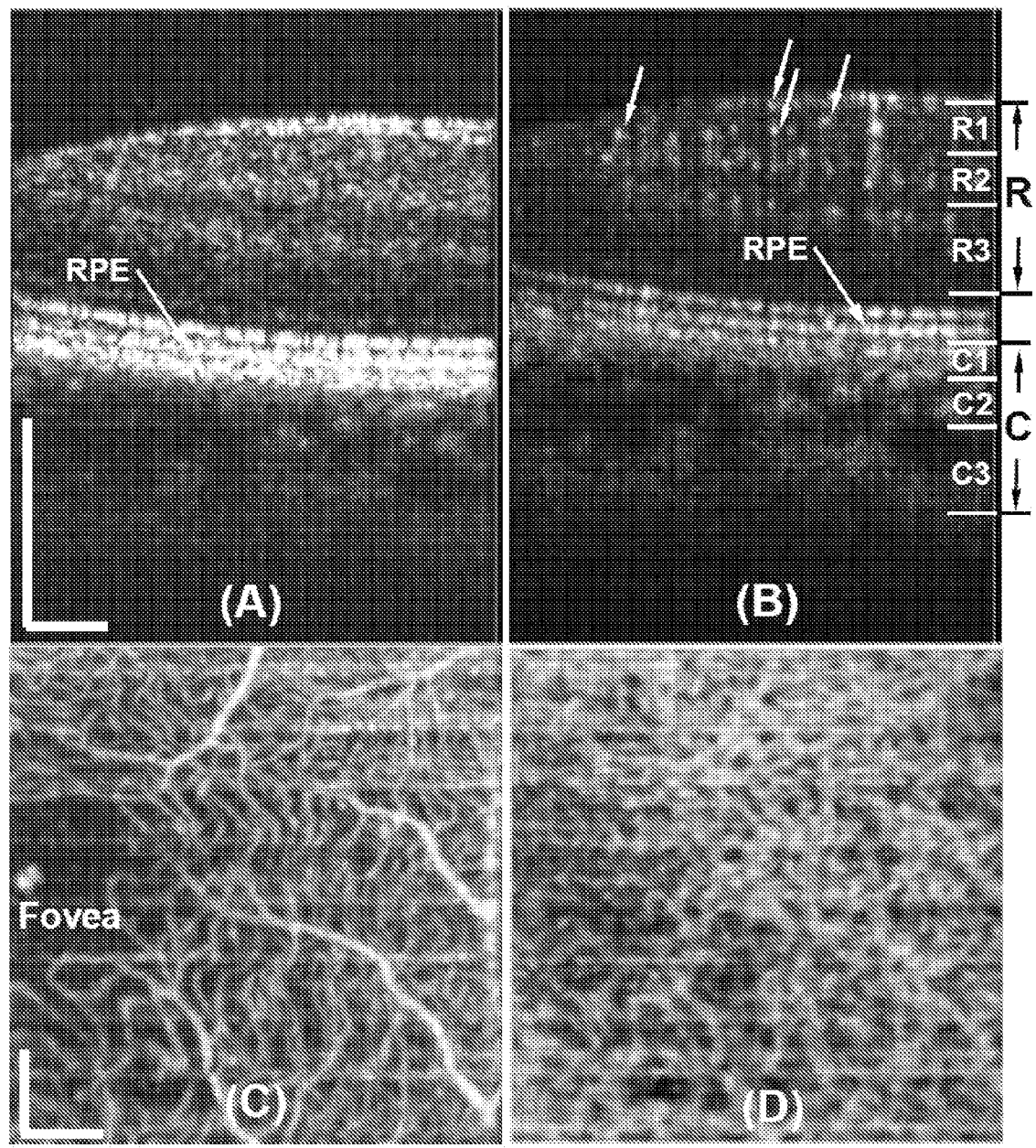
FIGS. 11A-D

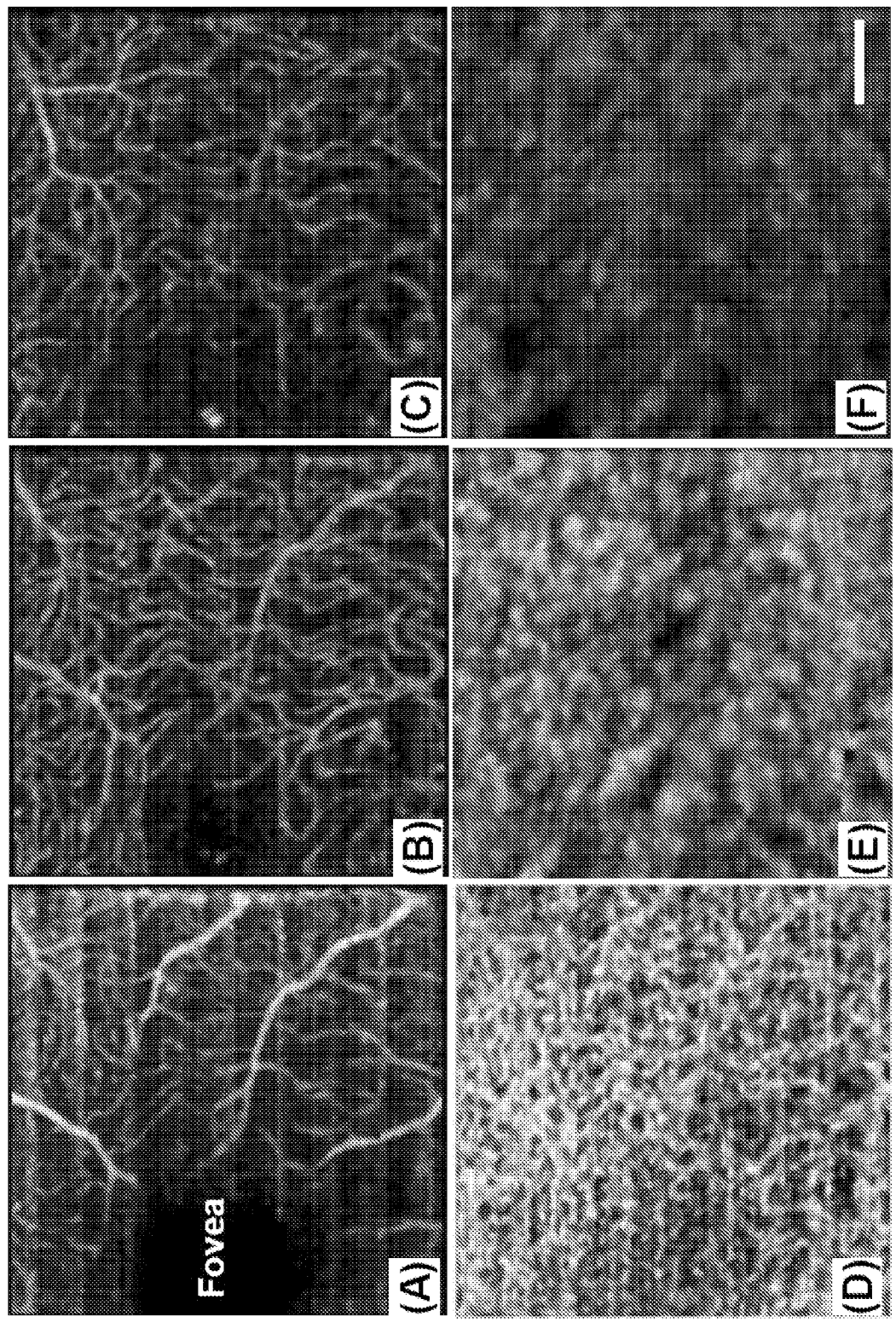
FIGS. 12A-F

METHOD AND APPARATUS FOR ULTRAHIGH SENSITIVE OPTICAL MICROANGIOGRAPHY

CROSS REFERENCE TO RELATED APPLICATIONS

The present application claims priority to U.S. Provisional Patent Application No. 61/302,409, filed Feb. 8, 2010, entitled "Method and Apparatus for Ultrahigh Sensitive Optical Microangiography," the entire disclosure of which is hereby incorporated by reference in its entirety.

The present application is related to U.S. Provisional Patent Application No. 61/175,229, filed May 4, 2009, entitled "Method and Apparatus for Quantitative Imaging of Blood Perfusion in Living Tissue" and Publication No. WO2008/039660, filed Sep. 18, 2007, entitled "In Vivo Structural and Flow Imaging," the entire disclosures of which are hereby incorporated by reference in their entirety.

GOVERNMENT INTERESTS

This invention was made with Government support under Grant/Contract No. R01HL093140, R01EB009682 and R01DC010201 awarded by the US National Institute of Health. The Government has certain rights in the invention.

TECHNICAL FIELD

Embodiments herein relate to the field of imaging, and, more specifically, to a method and apparatus for ultrahigh sensitive optical microangiography.

BACKGROUND

The assessment of blood flow in living tissue provides important information for diagnostics, treatment and/or management of pathological conditions. For example, the assessment of cutaneous (skin) microcirculations may provide important information for pathological conditions in dermatology, such as skin cancer, port wine stain treatment, diabetes, and plastic surgery. Similarly, assessment of the ocular perfusion within the retina and choroid of the human eye is important in the diagnosis, treatment, and management of a number of pathological conditions in ophthalmology, such as age-related macular degeneration, diabetic retinopathy, and glaucoma. Accordingly, clinical and technical tools that can noninvasively image three dimensional (3D) micro-blood vessel networks in vivo are in demand.

Several techniques have been developed to meet this need. However, current techniques suffer from various shortcomings which make them unsuitable for in vivo imaging in humans, such as low sensitivity to blood flow, insufficient resolution to provide useful depth information, and/or a long data acquisition time.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIGS. 5A-C show images of capillaries within human dermis, taken with a ultrahigh sensitive optical microangiography (UHS-OMAG) system according to various embodiments: (A) a Fourier domain optical coherence tomography (FDOCT) structural image; (B) a UHS-OMAG flow image; and (C) a phase resolved optical Doppler tomography (PRODT) cross-sectional flow image from the UHS-OMAG image of FIG. 5B;

FIGS. 5D-E show images of capillaries within human dermis, taken with a prior optical microangiography (OMAG) system, for comparison with the images in FIGS. 5A-C: (D) a Fourier domain optical coherence tomography (FDOCT) structural image; (E) an OMAG flow image; and (F) a phase resolved optical Doppler tomography (PRODT) cross-sectional flow image from the OMAG image of FIG. 5E;

FIG. 6A is a B-scan structural image of a flow phantom, and FIG. 6B is a corresponding UHS-OMAG flow image, in accordance with various embodiments.

FIG. 7A is a velocity image obtained from a flow phantom assessed by UHS-OMAG, in accordance with various embodiments;

FIG. 7B is a plot of the velocity data across the capillary tube at the position shown as the horizontal line in FIG. 7A, in accordance with various embodiments;

FIG. 7C and FIG. 7D are the corresponding results to FIGS. 7A and 7B, respectively, obtained by PRODT imaging of the same phantom, in accordance with various embodiments;

FIG. 8A is a schematic diagram of the blood vessel system of the human skin;

FIG. 8B is a photograph of a palm showing the scanning area;

FIG. 8C is a three dimensional (3D) rendered OMAG image of blood vessels together with the 3D structures, in accordance with various embodiments;

FIG. 8D is a cross sectional view of the imaged blood vessels, in accordance with various embodiments;

FIGS. 9A-D show UHS-OMAG detailed projection views of microcirculation network at different depths of skin obtained from: (A) 400-450 μm (closely representing papillary dermis); (B) 450-650 μm; (C) 650-780 μm (closely representing reticular dermis); and (D) 780-1100 μm (part of hypodermis), respectively, in accordance with various embodiments;

FIGS. 11A-B show in vivo UHS-OMAG imaging, in accordance with various embodiments, of the posterior segment of eye near the macular region towards the optic nerve head: (A) an OMAG B-scan of microstructures showing morphological features, and (B) the corresponding OMAG blood flow image;

FIGS. 11C-D show projection maps of blood flow distribution within: (C) retina and (D) choroid, obtained from one 3D scan of an area of ~3×3 mm² near the macular region, in accordance with various embodiments; and FIGS. 12A-F show depth-resolved images, in accordance with various embodiments, of patent blood vessels within the retina (FIGS. 12A-C) and choroid (FIGS. 12D-F) at the landmarked depths annotated in FIG. 11B: (A) R1—beyond 425

Figure 1:
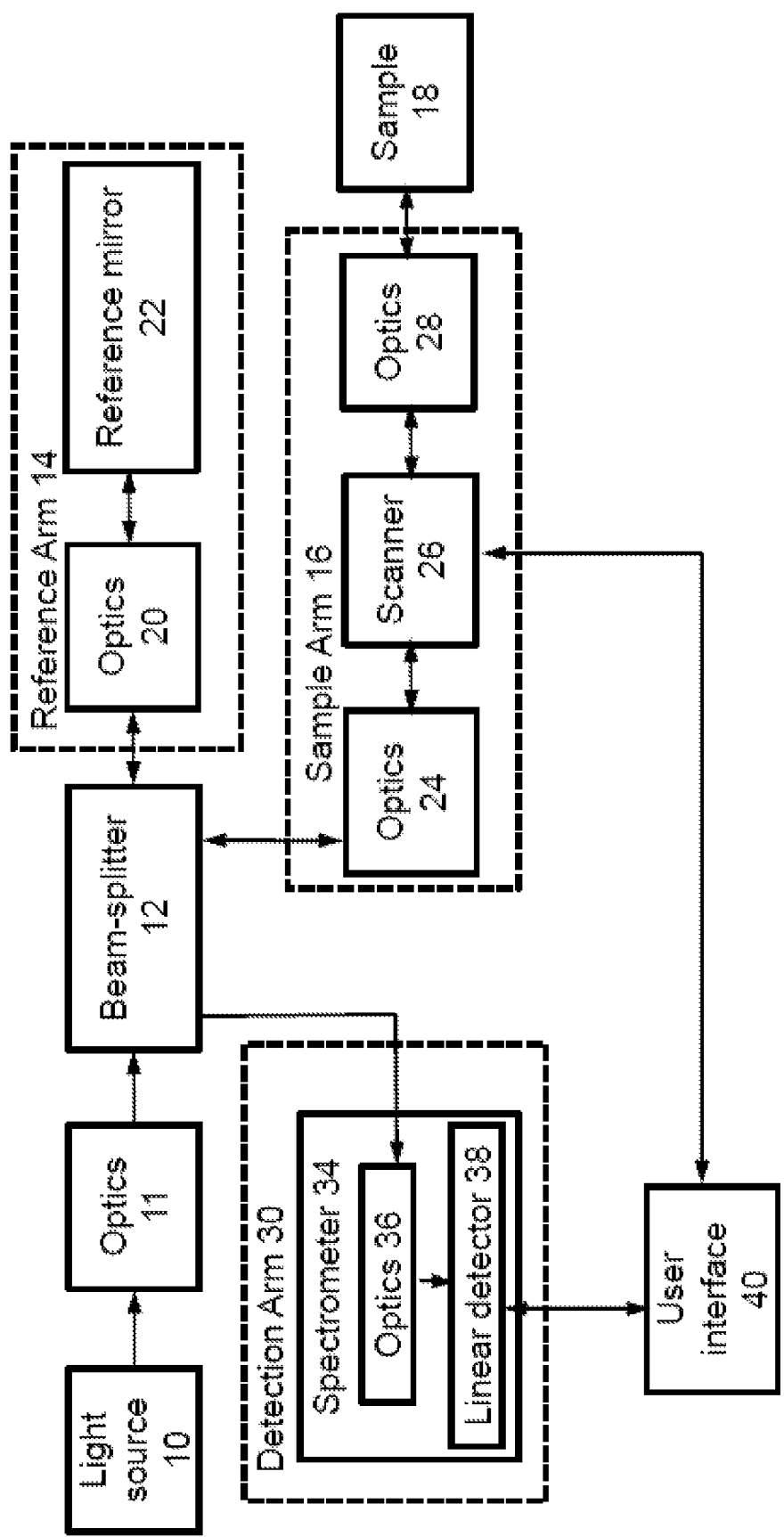
FIG. 1 illustrates a functional block diagram of an imaging apparatus in accordance with various embodiments of the present invention

μm above RPE; (B) R2—between 300 and 425 μm above RPE; (C) R3—between 50 and 300 μm above RPE; (D) C1—between 0 to 70 μm below RPE; (E) C2—between 70 to 200 μm below RPE; and (F) C3—beyond 200 μm below RPE.

DETAILED DESCRIPTION OF DISCLOSED EMBODIMENTS

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "NB" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

In various embodiments, methods, apparatuses, and systems for ultrahigh sensitive optical microangiography (UHS-OMAG) are provided. In exemplary embodiments, a computing device may be endowed with one or more components of the disclosed apparatuses and/or systems and may be employed to perform one or more methods as disclosed herein.

Embodiments herein provide an UHS-OMAG system that delivers high sensitivity with a relatively low data acquisition time. OMAG is an imaging modality that is a variation on optical coherence tomography (OCT). The imaging is based on the optical signals scattered by the moving particles. The light backscattered from a moving particle may carry a beating frequency that may be used to distinguish scattering signals by the moving elements from those by the static elements. Accordingly, OMAG can be used to image the flow of particles, such as blood flow.

Various embodiments of the UHS-OMAG system may include a light source, a sample arm, a reference arm and a detection arm. Illustrated in FIG. 1 is an exemplary embodiment of an UHS-OMAG apparatus 100 suitable for ultrahigh sensitive 2-D and 3-D flow imaging. The illustrated UHS-OMAG apparatus 100 may include some features known in the art, features which may not be explained in great length herein except where helpful in the understanding of embodiments of the present invention.

As illustrated, UHS-OMAG apparatus 100 may include a light source 10. Light source 10 may comprise any light source suitable for the purpose including, but not limited to, a broadband light source or a tunable laser source. A suitable broadband light source 10 may include a superluminescent diode. In one embodiment, light source 10 comprises a superluminescent diode with a central wavelength of 1310 nanometers (nm) and a full-width-at-half-maximum bandwidth of 65 nm. In various embodiments, light source 10 may be a light source having one or more longer/shorter wavelengths, which may allow for deeper imaging. In various other embodiments, light source 10 may comprise a tunable laser source such as, for example, a swept laser source.

UHS-OMAG apparatus 100 may include optics 11 to couple the light from the light source 10 into the system. The apparatus 100 may include a beam splitter 12 for splitting the light from the optics 11 into two beams: a first beam provided to a reference arm 14 and a second beam provided to a sample arm 16. In various embodiments, optics 11 may include, but are not limited to, various lenses or fiber optics components suitable for the purpose. Beam splitter 12 may comprise a 2×2 single-mode fiber coupler or any fiber coupler suitable for the purpose.

Reference arm 14 may be configured to provide a reference light to a detection arm 30 (discussed more fully below), from the light provided by light source 10, for producing a spectral interferogram in combination with backscattered light from sample 18. Reference arm 14 may include optics 20 and a mirror 22 for reflecting light from light source 10 for providing the reference light. Optics 20 may include, but are not limited to, various lenses suitable for the purpose.

Mirror 22 may be stationary or may be modulated. Modulation may be equivalent to frequency modulation of the detected signal at detection arm 30. It has been observed that spectral interference signals (interferograms) may be modulated by a constant Doppler frequency by a modulated mirror 22 in the reference arm 14. The spectral interference signal may then be recovered by de-modulating the modulated signal at the modulation frequency. De-modulation may be achieved using any suitable method including, for example, a digital or optical de-modulation method. Modulation and de-modulation of spectral interference signals may advantageously improve the signal-to-noise ratio, resulting in an improved image quality for structural, flow, and angiographic imaging.

Sample arm 16 may be configured to provide light from light source 10 to a sample 18 by way of optics 24, a scanner 26, and optics 28. Optics 24 may be used to couple the light from beam splitter 12 to scanner 26. Optics 24 may include various optical lens, for example an optical collimator. Scanner 26 may include a pair of x-y galvanometer scanners for scanning sample 28 in an x-y direction. Optics 28 may comprise the appropriate optics for delivering the light from the scanner 26 onto sample 18. In various embodiments, scanner 26 may also receive backscattered light from sample 18. Although the characteristics of the light provided to sample 18 may depend on the particular application, in some embodiments, the lateral imaging resolution may be approximately 16 micrometers (μm) determined by an objective lens that focuses light onto sample 18, with a light power on sample 18 being approximately 1 milliwatt (mW).

The light returning from reference arm 14 and the light returning from sample arm 16 (i.e., the spectral signal) may be recombined and coupled into the beam splitter 12 for introduction to detection arm 30. As illustrated, detection arm 30 comprises a spectrometer 34 including one or more of various optics 36 including, but not limited to, one or more collimators, one or more diffracting/transmission gratings, and one or more lenses (not illustrated). In exemplary embodiments, optics 36 may include a 30-millimeter (mm) focal length collimator, a 1200 lines/mm diffracting grating, and an achromatic focusing lens with a 150 mm focal length. In various embodiments, spectrometer 34 may have a designed spectral resolution of, for example, 0.055 nm, resulting in an optical range of approximately 6.4 mm in air, where the positive frequency space is 3.2 mm and the negative frequency space is 3.2 mm. Such parameters are exemplary and may be modified in a variety of ways in accordance with the embodiments of the present invention.

In embodiments employing a broadband light source, spectrometer 34 may include a detector such as a linear detector 38 configured to detect a spectral interference signal. Linear detector 38 may include one or more of a line-scan camera and an area scan camera. An exemplary suitable linear detector 38 may be a charge-coupled device (CCD).

In embodiments wherein light source 10 comprises a tunable laser rather than a broadband light source, however, UHS-OMAG apparatus 100 may include a diffusion amplifier that may comprise one or more single element detectors rather than spectrometer 34. For example, one or more dual-balanced photo-diode detectors may be used.

In various embodiments, reference arm 14, sample arm 16, and detection arm 30 may include polarization controllers (not illustrated). Polarization controllers may be configured to fine-tune the polarization states of light in UHS-OMAG apparatus 100. Although an UHS-OMAG apparatus within the scope of the present invention may include more or less polarization controllers, inclusion of polarization controllers in reference arm 14, sample arm 16, and detection arm 30, respectively, may advantageously maximize the spectral interference fringe contrast at linear detector 38 (or another suitable detector).

In various embodiments, UHS-OMAG apparatus 100 may include one or more user interfaces 40 for one or more purposes including controlling linear detector 38 and scanner 26, computing data using algorithms, displaying images, input of data, and/or output of data, etc.

As noted above, UHS-OMAG apparatus 100 may be configured to build a 3-D data volume set by scanning sample 18 with a sample light in x, y, and λ (z) directions to obtain a 3-D spectral interferogram data set.

In various embodiments, the scanner 26 may include an x-scanner and a y-scanner. During the composite scan, the x-scanner may perform at least one fast scan along a fast scan axis, and the y-scanner may perform at least one slow scan along a slow scan axis. The fast scan axis may be orthogonal to the slow scan axis (i.e., the fast scan axis and slow scan axis may define an x-y plane). The fast scan may also be referred to herein as a B-scan, and the fast scan axis may also be referred to as the x-axis, the lateral axis, and/or the B-scan axis. Similarly, the slow scan may also be referred to herein as a C-scan, and the slow scan axis may also be referred to as the y-axis, the elevational axis, and/or the C-scan axis. Each fast scan may be performed over a fast scan time interval, and each slow scan may be performed over a slow scan time interval, where the slow scan time interval is at least twice as long as the fast scan time interval. In some embodiments, the scanner may perform the one or more fast scans contemporaneously with the one or more slow scans. In such embodiments, a plurality of fast scans may be performed during one slow scan.

In each B-scan (fast scan), there may be a number, N, of A-scans. An A-scan may be performed in the z-axis, orthogonal to both the x-axis and the y-axis. Each A-scan may include a number, K, of pixels, i.e., data points, that provide imaging depth information in the z-axis. Similarly, a C-scan (slow scan) may include a number, M, of B-scans. In various embodiments, the numbers N, K, and M may be at least two. Accordingly, during a composite scan, a three-dimensional (3D) data set may be produced. The 3D data set may be represented as the complex function $I(x_i, y_j, z_k)$, where $i=1,2,\ldots N, j=1,2,\ldots, M$, and $k=1,2,\ldots, K$. In various embodiments, the magnitude portion of the 3D data set may be represented by the scalar function $A(x_i, y_j, z_k)$, where $I(x_i, y_j, z_k) = A(x_i, y_j, z_k)\exp(i\phi)$.

Figure 2:
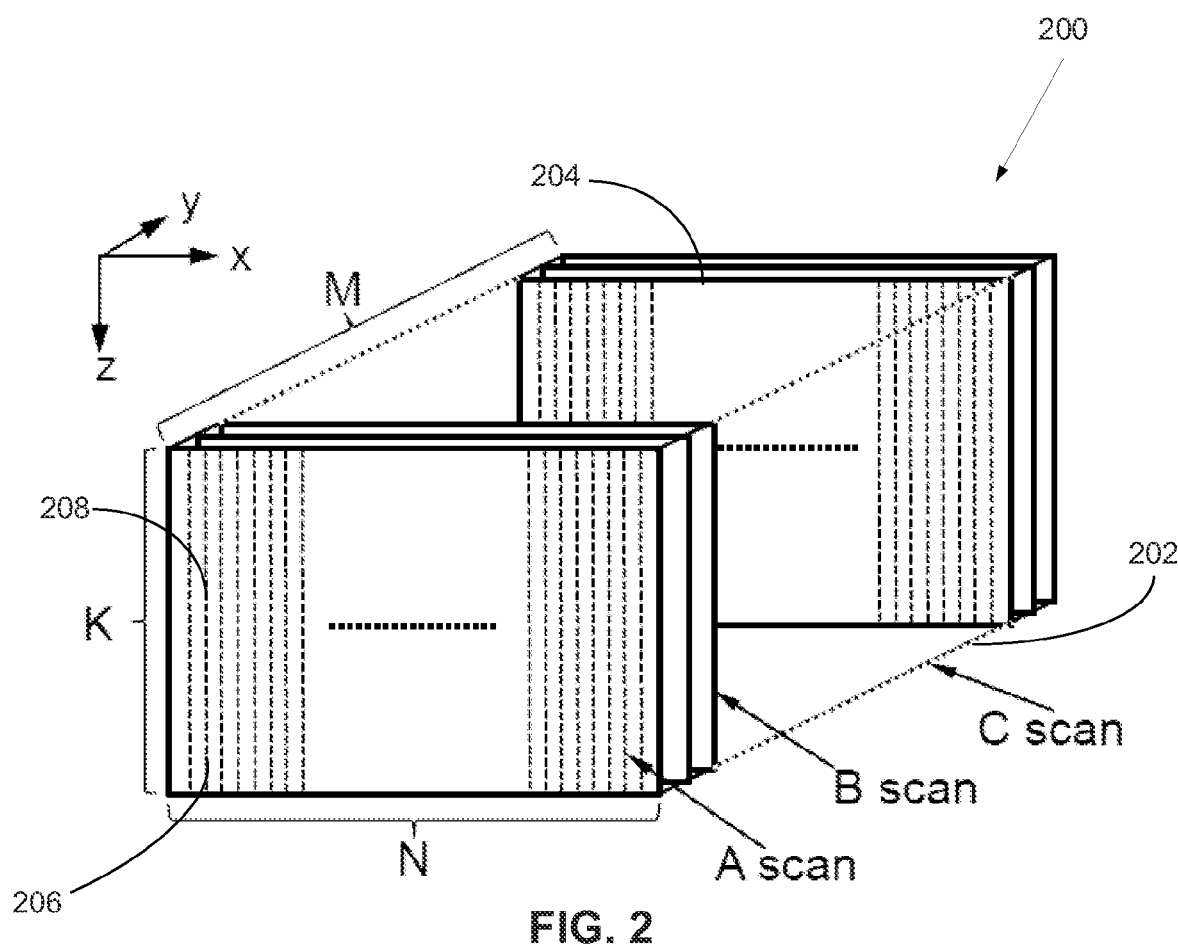
FIG. 2 illustrates an example of a 3D data set, in accordance with various embodiments.

FIG. 2 shows an example of a 3D data set 200 in accordance with various embodiments. Data set 200 includes one C-scan 202. C-scan 202 includes a number, M, of B-scans 204. Each B-scan 204 includes a number, N, of A-scans 206. Each A-scan 206 includes a number, K, of pixels 208, i.e., data points 208.

In various embodiments, an imaging algorithm may be applied to the 3D data set to produce at least one image. The imaging algorithm may be applied on the slow scan axis (i.e., y-axis). In some embodiments, the imaging algorithm may separate a moving component from a structural component of the sample. The image may be a full range structural image and/or a separated structural/flow image. In some embodiments, the image may be of blood flow, such as blood flow in a capillary and/or in a retina of an eye.

In this disclosure, reference is made to a prior OMAG method developed by the present applicants and described in Publication No. WO2008/039660, filed Sep. 18, 2007, entitled "In Vivo Structural and Flow Imaging," the entire disclosure of which is hereby incorporated by reference. As compared to the prior OMAG method, the embodiments herein provide a higher sensitivity and a lower data acquisition time. In some embodiments, the number, N, of A-scans in a B-scan may be decreased, while the number, M, of B-scans in a C-scan may be increased compared with the prior OMAG method. Additionally, the imaging algorithm is applied on the slow axis (i.e., C-scan axis, elevational axis), rather than on the fast axis (i.e., B-scan axis, lateral axis) as in the prior OMAG method. This provides a higher sensitivity to the moving component of the image (i.e., can image slower speeds), while providing a lower data acquisition time. A high data acquisition time may be unsuitable for in vivo use, since involuntary movement of the subject is unavoidable. Furthermore, additional imaging algorithms are provided herein that differ from the prior OMAG method, although imaging algorithms used in the prior OMAG method may also be used in some embodiments.

In the prior OMAG method, high pass filtering is normally applied in the B scan frames (obtained in the fast scanning axis) to isolate the optical scattering signals between the static and moving scatters. The detectable flow velocity, v, is thus determined by the time spacing, $\Delta t_A$, between the adjacent A scans, i.e., $v=\lambda/2n\Delta t_A$, where $\lambda$ is the central wavelength of the light source, and n is the refractive index of the sample. If a red blood cell moves along the probe beam direction at a speed, v, of less than or equal to 200 μm/s (i.e., v≤200 μm/s), then it would require a time spacing, $\Delta t_A$, of at least about 1.5 milliseconds (i.e., $\Delta t_A \geq$ ~1.5 milliseconds) for the system to sample the moving blood cell (assuming $\lambda$=840 nm and n=1.35). This time spacing translates into a scanning speed of about 643 A-scans/sec. Accordingly, the total imaging time to acquire a 3D capillary flow image of a tissue volume would be prohibitively long. The problem is exacerbated further under conditions where the probe beam is substantially perpendicular to the blow flow, such as when imaging the posterior segment of human eye, which makes the effective blood flow that is probed by the OMAG system very slow because the Doppler angle approaches 90 degrees.

In this disclosure, however, the algorithm is applied to the slow axis. Accordingly, the detectable flow signal is determined by the time spacing, $\Delta t_B$, between the adjacent B scans. In one exemplary embodiment, the B frame rate may be 300 Hz (see example one below), so $\Delta t_B$ may be about 3.3 milliseconds. In this case, the detectable flow would be about 140 μm/s, while the system scanning speed (i.e., A-scan rate) is not limited.

Accordingly, the total imaging time to acquire a 3D capillary flow image of a tissue volume would be dramatically reduced.

In various embodiments, the fastest flow that can be detected by the UHS-OMAG system may determined by the system imaging speed. In one exemplary embodiment, the imaging speed may have an A-scan rate of 47,000 per second (see example one below). Under this circumstance, the maximum detectable velocity may be about 30 mm/s.

In various embodiments, the slowest flow that can be detected by the UHS-OMAG system may be determined by the UHS-OMAG system phase noise floor. In one exemplary embodiment, with the imaging speed of 47,000 per second (see example one below), the system signal to noise ratio may be about 85 dB. The measured slowest detectable flow velocity may be about 4.0 μm/s.

In various embodiments, the x-scanner may be driven by a fast scan signal and the y-scanner may be driven by a slow scan signal. That is, the scanner may direct the probe beam along the fast scan axis and slow scan axis according to a property, such as a voltage, of the fast scan signal and the slow scan signal, respectively. The fast scan signal and slow scan signal may be any suitable waveforms, such as triangular, square, stepped, and/or sinusoidal.

Figure 3:
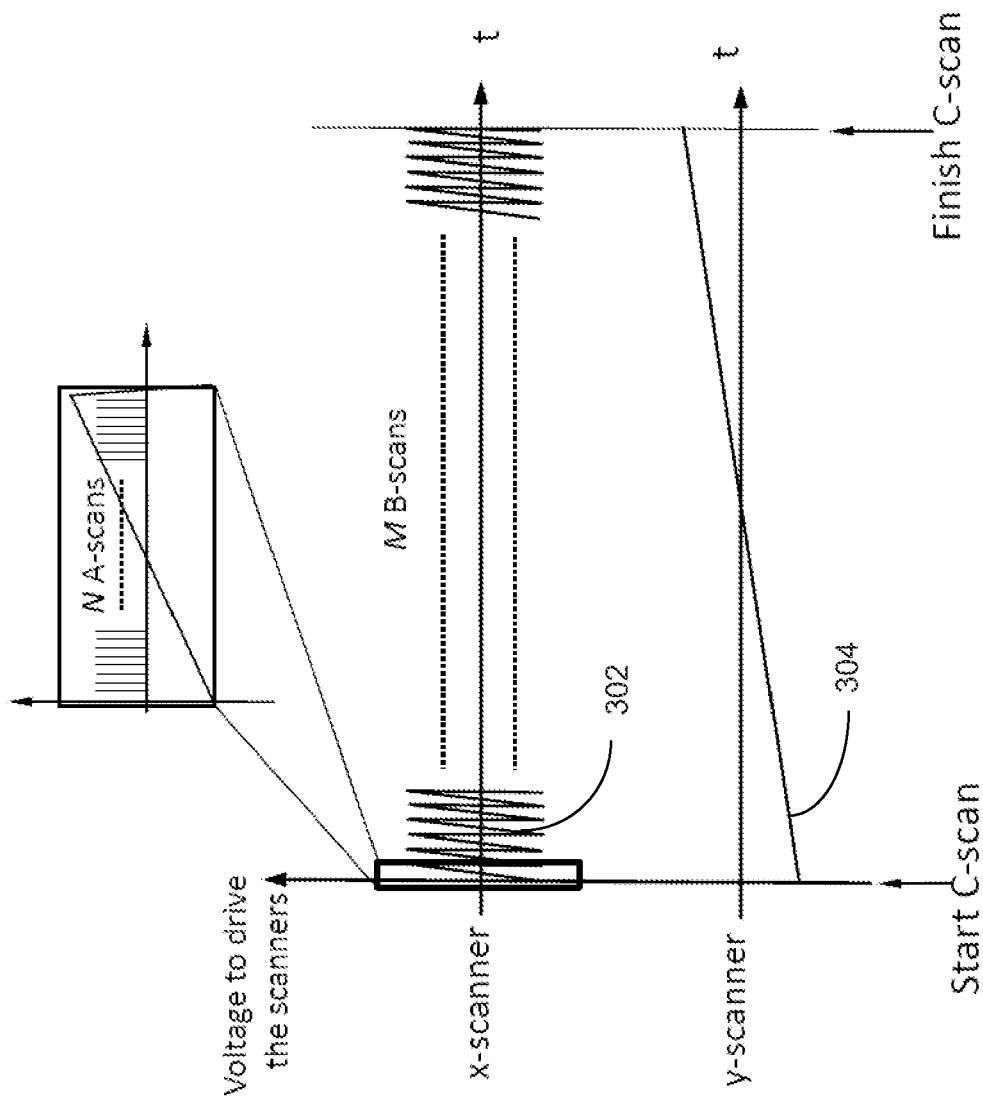
FIG. 3 illustrates an example of drive signals for an x-scanner and y-scanner, in accordance with various embodiments.

Any suitable scanning protocol may be used to combine the fast scan signal and slow scan signal to produce a suitable 3D data set. For example, FIG. 3 shows an embodiment where the fast scan signal 302 and slow scan signal 304 are each a triangular waveform (i.e., continuous scan). The fast scan signal 302 has a higher frequency than the slow scan signal 304. As the slow scan is performed to obtain a C-scan, a plurality of fast scans are performed to produce a plurality of B-scans. In some embodiments, only one slow scan may be performed in the composite scan, as depicted in FIG. 3. In other embodiments, a plurality of slow scans may be performed and combined into the composite scans.

Figure 4:
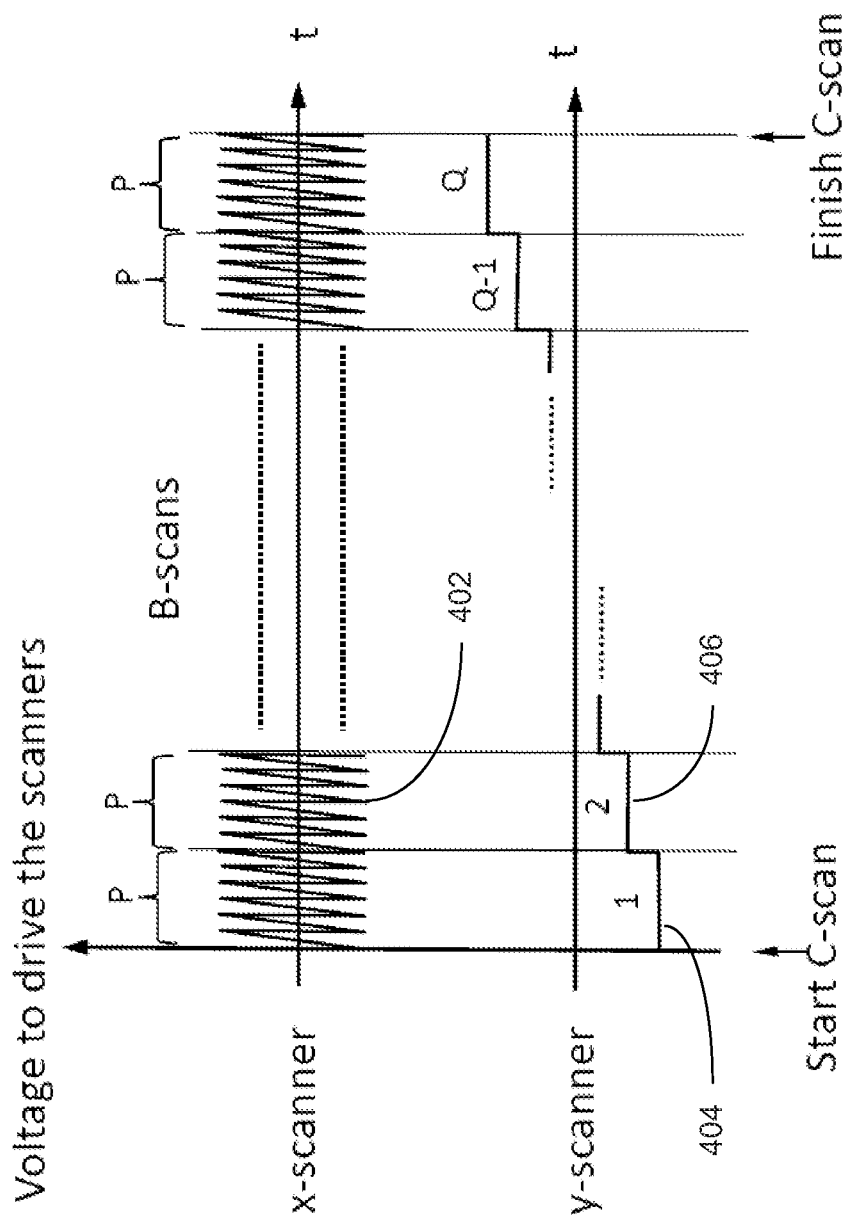
FIG. 4 illustrates another example of drive signals for an x-scanner and y-scanner, in accordance with various embodiments.

FIG. 4 shows an alternative embodiment, in which fast scan signal 402 is a triangular waveform, and slow scan signal 404 is a stepped waveform. The slow scan signal may have a number, Q, of steps 406 to finish one C-scan. At each step, a number, P, of B-scans may be acquired. Accordingly, the number, M, of B-scans in a C-scan may be P multiplied by Q (M=P×Q). In some embodiments, P may be at least two.

In various embodiments, any suitable imaging algorithm may be applied to the 3D data set to produce the image of the sample, such as a blood flow image. The imaging algorithm may be applied in the slow scan axis (i.e., the y-direction). The imaging algorithm may be designed to extract information on a moving component of the sample. Applying the imaging algorithm in the slow scan axis rather than the fast scan axis provides higher sensitivity, thereby allowing imaging of relatively slow movement, such as capillary blood flow within dermis which has typical flow in the range of about 100 to 900 μm/s in a resting condition, and even slower in diseased states.

In some embodiments, the imaging algorithm may include a differentiation operation in the y-direction, followed by an absolute operation. In some embodiments, the differentiation and absolute operations may be performed on the complex function $I(x_i, y_j, z_k)$ (i.e., $I'(x_i,y_j,z_k)=|I(x_i,y_j,z_k)-I(x_i,y_{j-1},z_k)|$ for j=1, 2, ..., M). In other embodiments, the differentiation and absolute operations may be performed on the magnitude portion $A(x_i, y_j, z_k)$ of the complex function $I(x_i,y_j,z_k)$ (i.e., $I'(x_i,y_j,z_k)=|A(x_i,y_{j-1},z_k)|$ for j=1, 2, ..., M)."

In other embodiments, the imaging algorithm may include a high pass filter that may be applied to the 3D data set in the y-direction (slow scan axis) in order to separate the optical signals scattered by the moving particles from the optical signal scattered by the microstructures, i.e., the static particles. The high pass filter may use any suitable type of high pass filtering function.

Furthermore, in some embodiments of the imaging algorithm, the prior OMAG method, as referenced above, may be applied to the 3D data set in the y-direction (slow scan axis).

In embodiments where M is large compared to N, i.e., B-scans are densely taken in the y-direction, averaging adjacent B-scans resulting from the imaging algorithm may improve the quality of final flow images. The number of B-scans used to average can be any number larger than, or equal to, 2.

In embodiments where the y-scanner is driven by a stepped function (as depicted in FIG. 4), the imaging algorithm may be applied independently at each step. Then, the image at each step (i.e., $1'(x_i,y_j,z_k)$), may be averaged to obtain a final B-scan image of the blood flow at that step. In some embodiments, the averaging may be done according to the following equation (Eq.(1)):

$$I(x_i, y_j,z_k)=[\Sigma_{j=1}^P I'(x_i,y_j,z_k)]/P, \text{ where } t=1,2, \ldots, Q \quad (1)$$

Accordingly, the final 3D image may include a number, Q, of B-scan images in the y-direction,"

In various embodiments, the algorithms described above may be applied to the 3D data set in the spectral/frequency domain (i.e., the data are in wavelength (or wavenumber) format). Further, in various embodiments, a logarithm operation may be applied to the 3D data set.

In various other embodiments, the algorithms described above may be applied to the 3D data set in the time/distance domain (i.e., the data are in time (or distance) format). In frequency/spectral domain optical coherence tomography, it has been observed that the time/distance domain signal and the spectral/frequency domain signal are a Fourier transform pair.

Example 1

Imaging Cutaneous Blood Flow at Capillary Level within Dermis

Below are a description and results of an experiment conducted using a UHS-OMAG system, in accordance with various embodiments, as applied to imaging capillary blood flows within dermis. Ideally, an imaging tool for such an application must be able to resolve the capillary blood flows within dermis, which are normally very slow (in the range of about 100 to 900 μm/s at the resting condition, and even slower at diseased states). In addition, such tools must be able to provide depth information with an imaging resolution at a scale of capillary blood vessel (about 10 μm). Furthermore, the imaging tool must have a relatively low data acquisition time to allow in vivo use, since involuntary movement of the subject is unavoidable.

The system setup for UHS-OMAG used in the experiment is similar to that described in R. K Wang, and L. An, "Doppler optical micro-angiography for volumetric imaging of vascular perfusion in vivo," *Opt. Express* 17, 8926-8940 (2009) (hereinafter "Article 1"), which is hereby incorporated by reference in its entirety. Here, the main parameters are briefly described. The system used a superluminescent diode as the light source, which has a central wavelength of 1310 nm and a bandwidth of 65 nm that provided an axial resolution in air of about 12 μm. In the sample arm, a 50 mm focal length objective lens was used to achieve a lateral resolution of about 16 μm. The output light from the interferometer was routed to a home-built spectrometer, which had a designed spectral resolution of about 0.141 nm that provided a detectable depth range of about 3 mm on each side of the zero delay line. The line scan rate of the camera was 47,000 per second (47kHz). With this imaging speed, the signal to noise ratio was measured at about 85 dB with a light power on the sample of about 3 mW.

The system applied a scanning protocol, similar to FIG. 3 (as discussed above), that was designed to achieve ultrahigh sensitive imaging to the blood flow. First, for each B-scan (i.e. x-direction scan), 128 A-lines were acquired with a spacing of about 15 μm between adjacent lines, thus covering a length of about 2 mm on the tissue. The imaging rate was 300 frames per second (fps). Note that with a 47 kHz line scan rate, the theoretical imaging rate should be 367 fps. The reduced imaging rate at 300 fps was due to data transfer limitations during the handshake between the camera and the computer.

Secondly, in the y-direction (i.e. C-scan direction), 1500 B-scans were captured over 2.0 mm on the tissue, which gave a spacing of about 1.3 μm between adjacent B-scans, equating to an oversampling factor of about 12 in the C-scan direction. The whole 3D data set was captured within 5 seconds.

The imaging algorithm was applied on the slow axis (C-scan direction) rather than the fast axis (B-scan direction). As discussed in Article 1, the interference signal of one B-scan captured by the CCD camera can be expressed as the following equation (Eq. (2)):

$$I(t,k)=2S(k)E_R[\int_{-\infty}^{\infty} a(z,t)\cos(2kn(t)z)dz + a(z_1)\cos[2kn(t)(z_1-vt)]] \quad (2)$$

where k is the wavenumber; t is the timing when an A-line was captured; $E_R$ is the light reflected from the reference mirror; S(k) is the spectral density of the light source used; n is the refractive index of tissue; z is the depth coordinate; a(z, t) is the amplitude of the back scattered light; v is the velocity of moving blood cells in a blood vessel, which is located at depth $z_1$. The self cross-correlation between the light backscattered from different positions within the sample is not considered in Eq. (2), because the light backscattered from the sample is weak compared to the light reflected from the reference mirror. Additionally, the DC signals are not considered, because they do not contribute to useful OMAG signals.

Prior OMAG systems used high pass filtering in the fast scanning axis, i.e. B-scan direction, to isolate the optical scattering signals between the static and moving scatters. Thus, the detect-able flow velocity, v, is determined by the time spacing, $\Delta t_A$, between the adjacent A-scans, i.e., $v=\lambda/2n\Delta t_A$, wherein λ is the central wavelength of the light source, and n is the refractive index of the sample. If the flow velocity in a capillary is less than or equal to 100 μm/s, then it would require $\Delta t_A$ to be greater than or equal to 4.7 ms for the system to have a chance to sample the blood cells flowing in the capillary. This time spacing translates into a scanning speed of about 213 A-scans per second. Therefore, the total data acquisition time to acquire a 3D capillary flow image of a tissue volume would be prohibitively long, and not ideal for in vivo imaging of capillary blood flows.

In order to image the slow blood flow within capillary vessels while keeping the data acquisition time low, the imaging algorithm is performed in the C-scan direction (slow scan axis). In this case, Eq. (2) can still be used to represent the spectral interferogram signal captured by the system, except that the time variable, t, now corresponds to the B-scan numbers in one C-scan. With this modification, the requirement of oversampling in the B-scan direction, as was present in the prior OMAG system, is relaxed, making it possible to have a much faster B-scan imaging rate, provided that the line scan camera in the spectrometer is limited or fixed. The detectable flow velocity is determined by the time spacing, $\Delta t_B$, between adjacent B-scans, i.e., $v=\lambda/2n\Delta t_B$. In the system setup described here, the imaging rate is 300 fps, so $\Delta t_B$ is about 3.3 ms. Note that the imaging speed is at 47,000 A scans per second, in contrast to 213 A scan per second required for prior OMAG method.

In the data processing, the imaging algorithm first takes a differential operation on the captured B-scan spectral interferograms along the C-scan direction, as in the following equation (Eq. (3)):

$$I_{flow}(t_i,k)=I(t_i,k)-I(t_{i-1},k), i=1,2,3 \ldots 1500 \quad (3)$$

where i represents the index of the B-scans in the C-scan direction. The differential operation suppresses the optical scattering signals from the static elements within scanned tissue volume. Alternatively, high pass filtering may be used. Then, a fast Fourier transform (FFT) is applied upon every wavenumber k (t is now constant) of Eq. (2) to obtain a depth-resolved OMAG flow image with ultrahigh sensitivity to the flow.

The minimum detectable blood flow is determined by the system phase noise floor, which can be expressed by the intensity signal to noise ratio, S, of the OMAG/OCT system by $\sigma_{\Delta\varphi}^2=1/S$. Thus, with the system signal to noise ratio at 85 dB, the minimum detectable flow velocity would be about 4.0 μm/s. However, if a blood cell moves at 4 μm/s, the system described here would not provide a continuous trajectory for this blood cell in the 3D OMAG flow image, i.e., the trajectory would be seen as a broken line.

Because the system is very sensitive to movement, the bulk motion of the sample may seriously degrade the final image result if the imaging algorithm is directly applied. To solve this problem, the phase compensation method described in Article 1 is applied to the raw interference signal before applying the OMAG algorithm.

To test the performance of the UHS-OMAG system described above for imaging blood flow, the system was tested on the skin located on the backside of a hand of a male volunteer. For comparison, the traditional OMAG and phase resolved optical Doppler tomography (PRODT) cross-sectional flow images were also obtained. For these methods, the system captured 2000 A-scans over 2 mm at an imaging speed of 31,000 A-scans per second in order to fulfill the oversampling requirement for these previous methods.

The results are shown in FIGS. 5A-F. The images in the top row (FIGS. 5A-C) are from the UHS-OMAG system while those in the bottom row (FIGS. 5D-F) are from the conventional prior OMAG system. FIGS. 5A and 5D are the Fourier domain optical coherence tomography (FDOCT) structural images obtained from the captured interferograms for the UHS-OMAG system and prior OMAG system, respectively. Although they are similar, they are not exactly the same due to the small subject movement when switching the system among the different approaches. However, it is sufficient to provide a fair comparison of their ability to extract slow flow information. FIG. 5B shows the image from FIG. 5A after it is processed by the UHS-OMAG system. FIG. 5C shows the PRODT image of the UHS-OMAG system, which is based on the phase difference between adjacent B-scans. Similarly, FIG. 5E shows the image from FIG. 5C after it is processed by the prior OMAG system. FIG. 5F shows the conventional PRODT image of the prior OMAG system, which is based on the phase difference between adjacent A-scans in one B-scan. In FIGS. 5C and 5F, the phase differences are calculated only when the structural signal is 15 dB above the noise floor.

It is apparent that the UHS-OMAG approach outperforms the other methods. FIG. 5B shows blood flows within the papillary dermis (indicated by white arrows), where only capillary blood vessels are present, as well as the blood flows within reticular dermis (indicated by red arrows), where both the capillary and larger blood vessels are present. By calculating the phase differences between adjacent B-scans, the blood flow velocities within the capillaries are within the reach of the UHS-OMAG (e.g., see the white arrows in FIG. 5C).

Because the conventional OMAG requires oversampling in the fast scanning direction (i.e., B-scan), it is not sensitive to the slow blood flow within the capillaries, which are normally below 100 µm/s. Accordingly, the conventional PRODT approach totally failed in imaging any of blood vessels, as seen in FIG. 5F. It should be noted that there is a global noise 'flow' background in the UHS-OMAG flow image, e.g., in FIG. 5B, which may be caused by some 'non-moving' scatters, such as global motion, etc. In this case, de-noising filters may be used to further enhance the UHS-OMAG flow imaging quality.

In order to test whether the flow sensitivity of UHS-OMAG approaches the system phase-noise floor (in this case about 4 µm/s as stated above), a second set of images was obtained using a highly scattering flow phantom as the imaging target. The phantom was made of gelatin mixed with about 1% milk to simulate the background optical heterogeneity of the tissue. In making this background tissue, precaution was taken so that the mixed gel was well solidified to minimize the possible Brownian motion of particles in the background. A capillary tube with an inner diameter of about 400 µm was submerged in this background tissue and about 2% $TiO_2$ particle solution was flowing in it that was controlled by a precision syringe pump. Although such setup can precisely control the flow velocity in the capillary tube, a flow speed as low as about 4 µm/s is difficult to provide. This is especially true considering that if the flow is stopped, the Brownian motion of particles is unavoidable in the capillary tube. With this experimental condition, the motion speed of particles due to Brownian motion would be randomly distributed within a range of several tens of microns per second. Due to these reasons, the experiments tested the UHS-OMAG system's ability to measure the Brownian motion of particles.

In the experiments, the capillary tube was made almost perpendicular to the incident sample beam to avoid free fall of the scattering particles within the tube. The imaging results are shown in FIGS. 6A-B. FIG. 6A is the OMAG/OCT microstructural image of the flow phantom, while FIG. 6B is the corresponding UHS-OMAG flow image. From this result, it is clear that UHS-OMAG is able to image the particle movements due to Brownian motion with almost no signals detected in the background region.

To examine in more detail, the phase-resolved technique was applied to the adjacent B-scans of the UHS-OMAG flow images to provide the velocity image of the flow phantom above. The result is shown in FIG. 7A, where it can be seen that the velocity values in the background region are low while those within the capillary tube are contrasted out primarily due to the Brownian motion of the particles. FIG. 7B shows a plot of the calculated velocities across the center of the capillary tube at the position marked as the horizontal line in FIG. 7A, where the dashed box indicates the position of the capillary lumen. The velocity values of particle movements ranged from approximately −50 to 100 µm/s at this cross-line position. The standard deviation of the values outside the dashed-box region was evaluated to be about 4.5 µm/s, which is close to the theoretical value of about 4 µm/s. This experiment concluded that the UHS-OMAG system is sensitive to the flow as low as about 4 µm/s for the system setup used in this study.

The conventional PRODT image was also obtained of the same phantom. In doing so, the system imaging rate was set at 31,000 A-scans per second. Additionally, the A-line density across the B-scan of about 2.5 mm was set at 4000, equating to a spacing between adjacent A-scans of about 0.625 µm. The corresponding results are given in FIGS. 7C and 7D, respectively, showing that PRODT totally failed to image the Brownian motion of the particles under the current experimental setup. Note that the standard deviation of velocity values shown in FIG. 7D was about 180 µm/s, thus it is not surprising that PRODT is not able to achieve satisfactory imaging performance.

After evaluation of the UHS-OMAG system's imaging performance, a subsequent experiment shows its capability to image the capillary blood flows within dermis in three dimensions. FIG. 8A shows a schematic drawing of the blood vessel system of the human skin, in which an interconnected network of vessels is characterized by regular structures on all levels. The human skin is composed of the cutis and the subcutis (hypodermis [HD]). The cutis is further divided into the epidermis (EP) and the dermis (DR). The dermis and subcutis are pervaded with a complex system of blood vessels, while the epidermis is free of vessels. A superficial network comprises the interface between papillary (PD) and reticular dermis (RD), while a lower network is located on the border between dermis and subcutis. Vertical vessels connect both networks and thus make it complete. In the diagram, arteries are shown in red and veins in blue. To show whether the ultrahigh sensitive OMAG is able to image the blood flow within the patent blood vessels as described above, 3D blood flow images were acquired over the palm of a healthy volunteer, as shown in FIG. 8B, where the black box indicates the scanning area (about 2×2 $mm^2$).

The 3D OMAG imaging result of blood vessel networks is shown in FIG. 8C, shown together with the 3D micro-structural image. FIG. 8D to shows a cross-sectional view, where the blood flows within blood vessel systems within the skin are clearly delineated. Because the UHS-OMAG sensitivity is as low as about 4 µm/s, even the dynamics of sweat glands are imaged.

The projection views at different land-mark depths are shown in FIGS. 9A-D. FIG. 9A gives the projection view at the depths from 400 to 450 µm, which corresponds to the papillary dermis where the capillary vessels are dense (e.g., indicated by the arrows). FIG. 9B shows the depths from 450 to 650 µm, where the vessels are almost vertical that connect vessel networks between papillary dermis and reticular dermis, seen as the bright spots in FIG. 9B. The blood vessel network in reticular dermis (650 to 780 µm) and hypodermis (780 to 1100 µm) are shown in FIGS. 9C and 9D, respectively. As shown, the vessel diameter is smaller in the reticular dermis than in the hypodermis. These observations from ultrahigh sensitive OMAG are almost identical to that described in the literature, demonstrating the power of the ultrahigh sensitive OMAG in the investigations of pathological conditions in dermatology.

These experiments demonstrated an ultrahigh sensitive OMAG system to image the volumetric microcirculation within the human skin. It was achieved by applying the OMAG algorithm along the slow scan axis (i.e., the C-scan direction), as opposed to the fast axis (i.e., the B scan direction). Comparing with the conventional OMAG flow image, the UHS-OMAG method delivers much better performance to extract slow flow information. Detailed 3D microvascular images obtained from the human skin by the UHS-OMAG system are comparable to those described in the standard textbook. Therefore, the ultrahigh sensitive OMAG may have great value in future clinical investigations of pathological conditions in human skin.

Example 2

Imaging of Capillary Networks in Retina and Choroid of Human Eye

Figure 10:
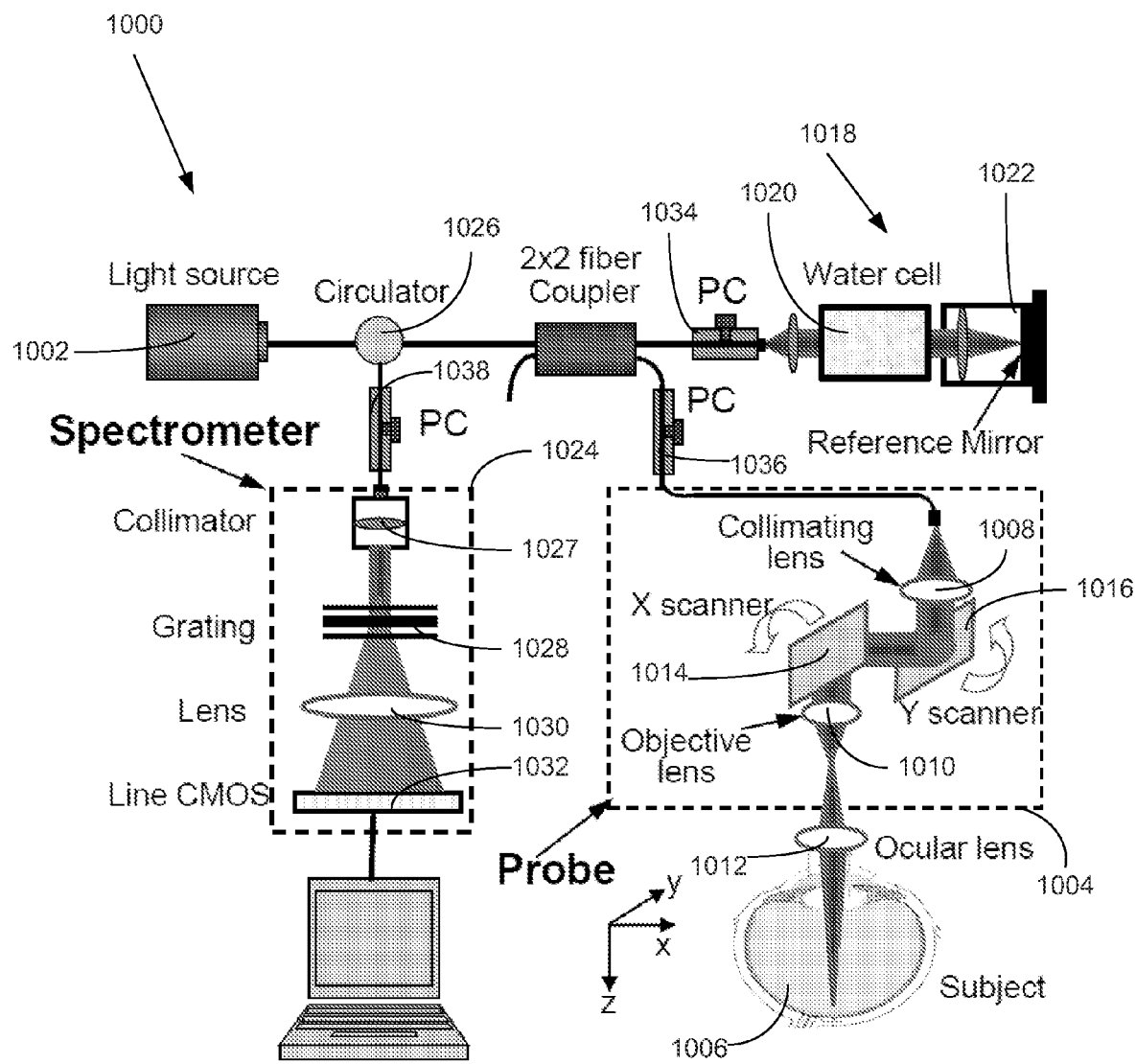
FIG. 10 shows a schematic diagram of a UHS-OMAG system, in accordance with various embodiments.

In another example, the UHS-OMAG system was used to obtain depth-resolved images of the capillary networks in the retina and choroid of the human eye. FIG. 10 shows the setup of the UHS-OMAG system 1000 used to obtain the images. The UHS-OMAG system 1000 is similar to that described in L. An, and R. K. Wang, *Optics Express*, 16, 11438-11452 (2008) (hereinafter "Article 2"). The UHS-OMAG system 1000 used includes a light source 1002 to produce a probe beam with a wavelength centered at 842 nm and a bandwidth of 46 nm that provided an axial resolution in air of about 8 µm. In a sample arm 1004, the light was delivered onto a human eye 1006 by a collimator 1008, an objective lens 1010, and an ocular lens 1012. The sample arm further includes an x-scanner 1014 and a y-scanner 1016 for scanning the human eye 1006 along the x-axis and y-axis, respectively.

In a reference arm 1018, a 20 mm water cell 1020 was used to compensate for the dispersion caused by the eye. A reference beam from the light source was reflected off a reference mirror 1022 to provide a reference light. An interferogram between the reference light and the light backscattered from the sample was sent to a home-built ultrafast spectrometer 1024 via an optical circulator 1026. The spectrometer included a collimator 1027, a transmission grating 1028 (with 1200 lines/mm), a camera lens 1030 with a focal length of 100 mm, and a 1024 element line scan CMOS detector 1032 capable of a 140 kHz line scan rate. The spectral resolution of the designed spectrometer 1024 was about 0.055 nm, which provided an imaging depth of about 3 mm in air. The system sensitivity was about 90 dB measured with about 900 µW power of light incident at the object and an exposure time of 6.9 µs with the time interval, $\Delta t_A$, between A-scans equal to about 7.4 µs. The system 1000 further includes polarization controllers 1034, 1036, and 1038 to control polarization of the light beam.

The UHS-OMAG system 1000 employed a scanning protocol, similar to FIG. 4 (as discussed above), designed to achieve ultrahigh sensitive imaging of the flow. Firstly, the x-scanner 1012 was driven by a 400 Hz sawtooth waveform, meaning that the imaging rate is 400 frames/sec (fps). The duty cycle for acquiring each B-scan (i.e., x-direction scan) was about 75%, in which we acquired 256 A-lines with a spacing of about 12 µm between adjacent lines that covered a size of about 3 mm on the retina. Secondly, the y-scanner was driven by a step function, and the entire C-scan includes 150 steps, with a spacing between adjacent steps of about 20 µm. In each step, 8 repeated B-scans were acquired. Accordingly, it required 3 seconds to acquire one 3D data set, covering an area of about 3×3 mm² on the retina.

An imaging algorithm was then applied on the 3D data set along the slow scan axis, i.e., C-scan direction. In this case, the detectable flow velocity is determined by the time spacing, $\Delta t_B$, between adjacent B-scans. Because the imaging speed was 400 fps, $\Delta t_B$=2.5 ms, which would be sufficient to image the slow flows in capillaries (see above). Finally, the calculated OMAG signals at each step were collapsed into one B-scan through ensemble-averaging (e.g., Eq.(1)), resulting in 150 B-scans to form the final C-scan image, i.e. 3D OMAG blood flow distribution.

To demonstrate the performance of the US-OMAG system, the system was used to obtain images on healthy volunteers. To reduce the eye and head movement, the volunteer was asked to steer at a fixed position during the experiment. FIGS. 11A-D show the in vivo imaging results produced by one volume dataset captured at the macular region towards the optic nerve head. FIG. 11A shows a typical cross-sectional image (B-scan) within the OMAG structural volume, which is identical to the conventional OCT image where the typical morphological features within retina and choroid are visualized. FIG. 11B gives the corresponding blood flow image obtained from the imaging algorithm, where the capillary flows within the cross-section of retina are abundant (indicated by arrows), as well as the blood flow signals in the choroid.

Because of the depth-resolved nature, the blood flows in the retina can be separated from those in the choroid. To do this, the segmentation algorithm described in Article 2 was first used to identify the retinal pigment epithelium (RPE) layer. Then, the flow signals from the retinal vessels were identified as the OMAG flow signals 50 µm above the RPE layer (to exclude the signals from photoreceptor inner and outer segments), while those below the RPE layer were identified as the choroidal vessels. The segmentation resulted in two volumetric flow images, one for retina and another for choroid, which are annotated in FIG. 11B by the labels of R and C, respectively. Finally, the maximum amplitude projection (MAP) was performed on each segmented retinal and choroidal volumes, giving the blood flow distribution maps shown in FIGS. 11C (retina) and 11D (choroid), respectively. In FIG. 11C, there is seen a ring of blood vessels in the macular area around an avascular zone about 800 µm in diameter, denoting the fovea. This observation is in excellent agreement with the standard retinal pathology.

According to the literature, the retina consists of three layers of capillary networks: the radial peripapillary capillaries (RPCs, R1) and an inner (R2) and an outer layer of capillaries (R3). The RPCs are the most superficial layer of capillaries lying in the inner part of the nerve fiber layer. The inner capillaries lie in the ganglion cell layers under and parallel to the RPCs. The outer capillary network runs from the inner plexiform to the outer plexiform through the inner nuclear layers. However, the choroidal vessels in the macular region are not specialized like those in the retina. The arteries pierce the sclera around the optic nerve and fan out to form three vascular layers in the choroid: inner capillary bed (near RPE layer, C1), medial arterioles and venules (C2) and outer arteries and veins (C3). With these descriptions as the reference, the OMAG blood flow signals obtained from the retinal and choroidal layers were further separated, with respect to the RPE layer. The segmentation is pictorially illustrated in FIG. 11B, with the labels of R1 (about 425 μm above RPE), R2 (between 300 and 425 μm above RPE) and R3 (between 50 and 300 μm above RPE) for retina, and C1 (from 0 to 70 μm below RPE), C2 (from 70 to 200 μm below RPE) and C3 (beyond 200 μm below RPE) for choroid, respectively. After segmentation, the blood flow MAPs within each land-marked depth are shown in FIGS. 12A-F (FIGS. 12A-C for retina and FIGS. 12D-F for choroid). The results are correlated well with the descriptions found in the literature.

The OMAG system running at 400 fps requires about 3 seconds to acquire one 3D blood flow image representing about 3×3 mm² area on the retina. At this speed, the effects of subject movement on the final results are clearly noticeable (the horizontal lines in FIGS. 11A-D and 12A-F are the motion artifacts). There may be several solutions to amend this problem, such as 1) the phase compensation algorithm developed in Article 2 may be used to minimize the motion artifacts before the imaging algorithm is applied. In doing so, however, it would inevitably increase the computational load required to obtain the meaningful 3D blood flow images because of the complexity of the compensation algorithms, and/or 2) the imaging speed may be further increased to minimize the motion artifacts. The current system speed is limited by the CMOS camera used in the spectrometer with a maximum line rate of 140 kHz. However, a report has shown that a 4096 element CMOS camera is capable of a line rate more than 240 kHz. Therefore, it would be expected that if this CMOS camera is used in the system, the motion artifacts may be mitigated.

As shown above, the UHS-OMAG system may be capable of imaging detailed ocular perfusion distributions within retina and choroid. Applying the imaging algorithm on the slow scanning axis, the system is sensitive to the ocular capillary flows. In addition, due to the depth-resolved nature, the system may be able to provide detailed micro-circulation within different land-marked depths, the results of which are in an excellent agreement with those described in the literature. The demonstrated superior imaging results show promise for future clinical applications for UHS-OMAG in ophthalmology.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method of imaging, comprising:
scanning a sample with a probe beam from a light source, the scanning including:
performing a plurality of fast scans (B-scans) on a fast scan axis, each fast scan comprising a plurality of A-scans;
performing one or more slow scans (C-scans), contemporaneously with the fast scans, on a slow scan axis, the slow scan axis being orthogonal to the fast scan axis, and each slow scan comprising a plurality of fast scans;
detecting one or more spectral interference signals from the sample during the scanning to generate a three dimensional (3D) data set, wherein the 3D data set is represented by the complex function $I(x_i, y_j, z_k)$; and
applying an imaging algorithm to the 3D data set along the slow scan axis to produce at least one image of the sample, wherein the imaging algorithm includes a differential operation of adjacent fast scans along the slow scan axis, the differential operation comprising $I'(x_i,y_j,z_k)=|I(x_i,y_j,z_k)-I(x_i,y_j,z_k)|$ for integer values of j from one to a number, M, of fast scans in a slow scan.

2. The method of claim 1, wherein the fast scans are driven by a first triangular waveform and the slow scans are driven by a second triangular waveform, the first triangular waveform having a higher frequency than the second triangular waveform.

3. The method of claim 1, wherein the slow scans are driven by a stepped waveform having a plurality of steps, and a plurality of fast scans are performed at each step of the stepped waveform.

4. The method of claim 1, wherein the imaging algorithm is configured to operate along the slow scan axis to separate a moving component of the sample from a structural component of the sample.

5. The method of claim 1, wherein the magnitude portion of the 3D data set is represented by the scalar function $A(x_i,y_j,z_k)$, where $I(x_i,y_j,z_k)=A(x_i,y_j,z_k)\exp(i\phi)$, and the differential operation comprises $I'(x_i,y_j,z_k)=|A(x_i,y_j,z_k)-A(x_i,y_{j-1},z_k)|$ for integer values of j from one to a number, M, of fast scans in a slow scan.

6. The method of claim 4, wherein the imaging algorithm comprises high pass filtering along the slow scan axis in the 3D data set.

7. The method of claim 1, wherein age of the sample comprises an image of a blood vessel network.

8. The method of claim 1, wherein the method is applied in vivo.

9. A system for in vivo imaging, comprising:
an optical micro-angiography (OMAG) apparatus; and
one or more processors coupled to the OMAG apparatus and adapted to cause the OMAG apparatus to:
scan a sample with a probe beam from a light source;
perform a plurality of fast scans (B-scans) on a fast scan axis, each fast scan comprising a plurality of A-scans;
perform one or more slow scans (C-scans), contemporaneously with the fast scans, on a slow scan axis, the slow scan axis being orthogonal to the fast scan axis, and each slow scan comprising a plurality of fast scans;
detect one or more spectral interference signals from the sample during the scanning to generate a three dimensional (3D) data set, wherein the 3D data set is represented by the complex function $I(x_i, y_j, z_k)$; and apply an imaging algorithm to the 3D data set along the slow scan axis to produce an image of the sample, wherein the imaging algorithm includes a differential operation of adjacent fast scans along the slow scan axis, the differential operation comprising $I'(x_i,y_j,z_k)=|I(x_i,y_j,z_k)-I(x_i,y_{j-1},z_k)|$ for integer values off from one to a number, M, of fast scans in a slow scan.

10. The system of claim 9, wherein the OMAG apparatus includes an x-scanner to perform the plurality of fast scans and a y-scanner to perform the one or more slow scans, and the x-scanner is driven by a fast scan signal, and the y-scanner is driven by a slow scan signal.

11. The system of claim 10, wherein the fast scan signal comprises a first triangular waveform and slow scan signal comprises a second triangular waveform, the first triangular waveform having a higher frequency than the second triangular waveform.

12. The system of claim 10, wherein the slow scan signal comprises a stepped waveform having a plurality of steps, and the fast scan signal is configured to cause the x-scanner to perform a plurality of fast scans during each step of the stepped waveform.

13. The system of claim 9, wherein the imaging algorithm is configured to operate along the slow scan axis to separate a moving component of the sample from a structural component of the sample.

14. The system of claim 9, wherein the magnitude portion of the 3D data set is represented by the scalar function $A(x_i, y_j, z_k)$, where $I(x_i,y_j,z_k)=A(x_i,y_j,z_k)\exp(i\phi)$ and the differential operation comprises $I'(x_i,y_j,z_k)=|A(x_i,y_j,z_k)-A(x_i,y_{j-1},z_k)|$ for integer values of j from one to a number, M, of fast scans in a slow scan.

15. The system of claim 13, wherein the imaging algorithm comprises high pass filtering along the slow scan axis in the 3D data set.

16. The system of claim 9, wherein the image of the sample comprises an image of a blood vessel network.

17. The system of claim 9, wherein the OMAG apparatus is a Fourier domain optical coherence tomography (FD-OCT) apparatus.

* * * * *

UNITED STATES PATENT AND TRADEMARK OFFICE
CERTIFICATE OF CORRECTION

PATENT NO. : 9,013,555 B2
APPLICATION NO. : 13/577857
DATED : April 21, 2015
INVENTOR(S) : Ruikang K. Wang It is certified that error appears in the above-identified patent and that said Letters Patent is hereby corrected as shown below:

In the Specification

At Column 1, Lines 24-27, under the heading GOVERNMENT INTERESTS, please delete the following:
"This invention was made with Government support under Grant/Contract No. R01HL093140, R01EB009682 and R01DC010201 awarded by the US National Institute of Health. The Government has certain rights in the invention."

And replace it with the following:
--This invention was made with government support under HL093140 awarded by The National Institutes of Health. The government has certain rights in the invention.--

Signed and Sealed this
Twenty-third Day of August, 2022

Katherine Kelly Vidal
*Director of the United States Patent and Trademark Office*